(12) United States Patent
Ciccarelli et al.

(10) Patent No.: US 11,630,513 B2
(45) Date of Patent: Apr. 18, 2023

(54) END-TO-END DEEP NEURAL NETWORK FOR AUDITORY ATTENTION DECODING

(71) Applicants: Massachusetts Institute of Technology, Cambridge, MA (US); The Trustees of Columbia University in the City of New York, New York, NY (US)

(72) Inventors: Gregory Ciccarelli, Cambridge, MA (US); Christopher Smalt, Arlington, MA (US); Thomas Quatieri, Newtonville, MA (US); Michael Brandstein, Acton, MA (US); Paul Calamia, Ashland, MA (US); Stephanie Haro, Cambridge, MA (US); Michael Nolan, Somerville, MA (US); Joseph Perricone, Nashville, TN (US); Nima Mesgarani, New York, NY (US); James O'Sullivan, New York, NY (US)

(73) Assignee: Massachusetts Institute of Technology, Cambridge, MA (US)

(*) Notice: Subject to any disclaimer, the term of this patent is extended or adjusted under 35 U.S.C. 154(b) by 642 days.

(21) Appl. No.: 16/720,810

(22) Filed: Dec. 19, 2019

(65) Prior Publication Data

US 2020/0201435 A1 Jun. 25, 2020

Related U.S. Application Data

(60) Provisional application No. 62/782,766, filed on Dec. 20, 2018.

(51) Int. Cl.
*G06F 3/01* (2006.01)
*G06K 9/62* (2022.01)
(Continued)

(52) U.S. Cl.
CPC .............. *G06F 3/015* (2013.01); *A61B 5/121* (2013.01); *A61B 5/31* (2021.01); *A61B 5/369* (2021.01);
(Continued)

(58) Field of Classification Search
None
See application file for complete search history.

(56) References Cited

U.S. PATENT DOCUMENTS 9,432,777 B2   8/2016  Lunner et al.
10,285,615 B2 * 5/2019  Kidmose ............... A61B 5/38
(Continued)

FOREIGN PATENT DOCUMENTS

CN   107705806 A  *  2/2018
CN   108236464 A  *  7/2018  ......... A61B 5/04845
(Continued)

OTHER PUBLICATIONS

Chou et al., A Physiologically Inspired Model for Solving the Cocktail Party Problem, Journal of the Association Otolaryngology, pp. 579-593 (Year: 2018).*

(Continued)

*Primary Examiner* — Mohammed Rachedine
(74) *Attorney, Agent, or Firm* — Daly, Crowley, Mofford & Durkee, LLP (57) ABSTRACT

In one aspect of the present disclosure, method includes: receiving neural data responsive to a listener's auditory attention; receiving an acoustic signal responsive to a plurality of acoustic sources; for each of the plurality of acoustic sources: generating, from the received acoustic signal, audio data comprising one or more features of the acoustic source, forming combined data representative of the neural data and the audio data, and providing the combined data to a classification network configured to (Continued)

calculate a similarity score between the neural data and the acoustic source using one or more similarity metrics; and using the similarity scores calculated for each of the acoustic sources to identify, from the plurality of acoustic sources, an acoustic source associated with the listener's auditory attention.

17 Claims, 6 Drawing Sheets

(51) Int. Cl.
| | |
|---|---|
| G06K 9/00 | (2022.01) |
| G06N 3/04 | (2023.01) |
| G06N 3/08 | (2023.01) |
| G10L 21/0208 | (2013.01) |
| G10L 21/0272 | (2013.01) |
| A61B 5/12 | (2006.01) |
| A61B 5/31 | (2021.01) |
| A61B 5/369 | (2021.01) |
| H04R 1/10 | (2006.01) |
| H04R 25/00 | (2006.01) |
| G06N 3/02 | (2006.01) |
| G06F 18/22 | (2023.01) |
| G06F 18/25 | (2023.01) |

(52) U.S. Cl.
CPC .............. *G06F 3/017* (2013.01); *G06F 18/22* (2023.01); *G06F 18/251* (2023.01); *G06N 3/02* (2013.01)

(56) References Cited

U.S. PATENT DOCUMENTS

| | | | |
|---|---|---|---|
| 2012/0177233 A1 | 7/2012 | Kidmose et al. | |
| 2018/0014130 A1* | 1/2018 | Lunner | A61F 11/06 |
| 2018/0049896 A1* | 2/2018 | Connolly | A61B 5/11 |
| 2019/0066713 A1 | 2/2019 | Mesgarani et al. | |
| 2019/0247662 A1* | 8/2019 | Poltroak | A61B 5/0816 |
| 2019/0295566 A1* | 9/2019 | Moghadamfalahi | A61B 5/318 |
| 2020/0005770 A1* | 1/2020 | Lunner | G06F 3/015 |

FOREIGN PATENT DOCUMENTS

| | | | | |
|---|---|---|---|---|
| CN | 106933345 B | * | 2/2020 | G06F 3/015 |
| EP | 3267698 A1 | | 10/2018 | |
| WO | WO 2017/218492 A1 | | 12/2017 | |

OTHER PUBLICATIONS

Abrams, et al. "An Introduction to MarkeTrak IX: a New Baseline for the Hearing Aid Market;" The Hearing Review; Jun. 2015; 6 Pages.

Aiken, et al. "Human Cortical Responses to the Speech Envelope;" Ear and Hearing, vol. 29, No. 2; Apr. 1, 2008; pp. 139-157; 19 Pages.

Akram, et al. "Robust decoding of selective auditory attention from MEG in a competing-speaker environment via state-space modeling;" NeuroImage, vol. 124, Part A; Jan. 1, 2016; pp. 906-917; 12 Pages.

Andrade, et al. "The silent impact of hearing loss: Using longitudinal data to explore the effects on depression and social activity restriction among older people;" Ageing & Society, vol. 38, Issue 12; Dec. 1, 2018; pp. 2468-2489; 22 Pages.

Andrew, et al. "Deep Cononical Correlation Analysis;" ICML 2013: Proceedings of the 30th International Conference on International Conference on Machine Learning; vol. 28; Jun. 2013; 9 Pages.

Arlinger, "Negative consequences of uncorrected hearing loss—a review;" International Journal of Audiology, vol. 42, Supp. 2; 2003; pp. 17-20; 5 Pages.

Aroudi, et al. "Auditory attention decoding with EEG recordings using noisy acoustic reference signals;" 2016 IEEE International Conference on Acoustics, Speech and Signal Processing (ICASSP); Mar. 20, 2016; pp. 694-698; 5 Pages.

Baltzell, et al. "Attention selectively modulates cortical entrainment in different regions of the speech spectrum;" Brain Research, vol. 1644; Aug. 1, 2016; pp. 203-212; 10 Pages.

Belouchrani, et al. "On the Use of Spatial Time Frequency Distributions for Signal Extraction;" Multidimensional Systems and Signal Processing; vol. 9; Oct. 1998; 6 Pages.

Biesmans, et al. "Auditory-inspired speech envelope extraction methods for improved EEG-based auditory attention detection in a cocktail party scenario;" IEEE Transactions on Neural Systems and Rehabilitation Engineering, vol. 25, No. 5, May 7, 2017; pp. 402-412; 11 Pages.

Bleiclmer, et al. "Identifying auditory attention with ear-EEG: cEEGrid versus high-density cap-EEG comparison;" Journal of Neural Engineering, vol. 13; Oct. 5, 2016; 14 Pages.

Chatteijee, et al. "Similarity learning with (or without) convolutional neural networks" Retrieved from http://slazebni.cs.illinois.edu/spring17/; Jan. 1, 2017; 75 Pages.

Clevert, et al. "Fast and accurate deep network learning by exponential linear units (ELUs);" Retrieved from https://arxiv.org/abs/1511.07289, Version 1; Nov. 23, 2015; 14 Pages.

Das, et al. "EEG-based auditory attention detection: Boundary conditions for background noise and speaker positions;" Journal of Neural Engineering, vol. 15; Oct. 9, 2018; 12 Pages.

Dau, et al. Towards cognitive control of hearing instruments using EEG measures of selective attention; The Journal of the Acoustical Society of America; vol. 143, Issue 3; Mar. 2018; 3 Pages.

De Cheveigné, et al. "Decoding the auditory brain with canonical component analysis;" NeuroImage; vol. 172, Jan. 31, 2018; 11 Pages.

De Taillez, et al. "Machine learning for decoding listeners' attention from electroencephalography evoked by continuous speech;" European Journal of Neuroscience; Dec. 4, 2017; 8 Pages.

De Taillez, https://github.com/tdetaillez/neural_networks_auditory_attention_decoding/blob/master/Code.py; Sep. 5, 2017; 6 Pages.

Deckers, et al. "EEG-based detection of the attended speaker and the locus of auditory attention with convolutional neural networks;" https://doi.org/10.1101/475673; Nov. 28, 2018; 16 Pages.

Ding, et al. "Neural coding of continuous speech in auditory cortex during monaural and dichotic listening;" Journal of Neurophysiology; vol. 107; Jan. 1, 2012; 12 Pages.

Fiedler, et al. "Single-channel in-ear-EEG detects the focus of auditory attention to concurrent tone streams and mixed speech;" Journal of Neural Engineering; vol. 14, No. 3; Apr. 6, 2017; 12 Pages.

Fuglsang, et al. "Noise-robust cortical tracking of attended speech in real-world acoustic scenes;" NeuroImage; vol. 156; Apr. 13, 2017; 10 Pages.

Golumbic, et al. "Mechanisms underlying selective neuronal tracking of attended speech at a 'cocktail party';" Neuron; Mar. 6, 2013; 24 Pages.

Gorgolewski, et al. "Nipype: a flexible, lightweight and extensible neuroimaging data processing framework in python;" Frontiers in Neuroinformatics; vol. 5, Article 13; Aug. 22, 2011; 15 Pages.

Horwitz-Martin, et al. "A vocal modulation model with application to predicting depression severity;" 2016 IEEE 13th International Conference on Wearable and Implantable Body Sensor Networks (BSN), Jun. 14, 2016; 7 Pages.

Ioffe, et al. "Batch normalization: Accelerating deep network training by reducing internal covariate shift;" arXiv:150203167; Mar. 2, 2015; 9 Pages.

Kam, et al. "Systematic comparison between a wireless EEG system with dry electrodes and a wired EEG system with wet electrodes;" NeuroImage; vol. 184; Jan. 1, 2019; 11 Pages.

Kochkin, "Customer satisfaction with hearing instruments in the digital age;" The Hearing Journal; vol. 58, No. 9; Sep. 1, 2005; 10 Pages.

Lesica, "Why Do Hearing Aids Fail to Restore Normal Auditory Perception?;" Trends in Neurosciences; vol. 41, No. 4; Apr. 2018; 12 Pages.

(56) References Cited

OTHER PUBLICATIONS

Luo, et al. "Conv-TasNet: Surpassing Ideal Time-Frequency Magnitude Masking for Speech Separation;" Retrieved from https://arxiv.org/pdf/1809.07454.pdf; May 15, 2019; 12 Pages.

Mendoza, et al. "Decoding Auditory Attention from Multivariate Neural Data using Cepstral Analysis;" Lund University, Dept. of Mathematical Statistics; Jun. 2018; 92 Pages.

Mener, et al. "Hearing loss and depression in older adults;" Journal of the American Geriatrics Society; vol. 61; Sep. 2013; 5 Pages.

Mesgarani, et al. "Selective cortical representation of attended speaker in multi-talker speech perception;" Nature; vol. 485; May 10, 2012; 5 Pages.

Miran, et al. "Real-time tracking of selective auditory attention from M/EEG: a bayesian filtering approach;" Frontiers in Neuroscience; vol. 12, Article 262; May 1, 2018; 20 Pages.

Mirkovic, et al. "Decoding the attended speech stream with multichannel EEG: Implications for online, daily-life applications;" Journal of Neural Engineering; vol. 12; Aug. 2015; 10 Pages.

O'Sullivan, et al. "Attentional selection in a cocktail party environment can be decoded from single-trial EEG;" Cerebral Cortex; vol. 25; Jul. 2015; 10 Pages.

O'Sullivan, et al. "Neural decoding of attentional selection in multi-speaker environments without access to separated sources;" Engineering in Medicine and Biology Society (EMBC), 2017 39th Annual International Conference of the IEEE; Jul. 2017; 4 Pages.

Paszke, et al. "Automatic differentiation in PyTorch;" 31st Conference on Neural information processing systems (NIPS); Dec. 4, 2017; 4 Pages.

Pedregosa, et al. "Scikit-learn: Machine Learning in Python;" Journal of Machine Learning Research; vol. 12; Dec. 2011; 6 Pages.

Srivastava, et al. "Dropout: a simple way to prevent neural networks from overfitting;" The Journal of Machine Learning Research; vol. 15; Jun. 2014; 30 Pages.

Tremblay, et al. "How neuroscience relates to hearing aid amplification. International Journal of Otolaryngology;" International Journal of Otolaryngology; vol. 2014; Article ID 641652; Jun. 18, 2014; 8 Pages.

USVA, "Annual Benefits Report Fiscal Year 2017;" US Department of Veterans Affairs, Veterans Benefits Administration; 2017; Part 1; 75 Pages.

USVA, "Annual Benefits Report Fiscal Year 2017;" US Department of Veterans Affairs, Veterans Benefits Administration; 2017; Part 2; 75 Pages.

USVA, "Annual Benefits Report Fiscal Year 2017;" US Department of Veterans Affairs, Veterans Benefits Administration; 2017; Part 3; 76 Pages.

Van Eyndhoven, et al. "EEG-informed attended speaker extraction from recorded speech mixtures with application in neuro-steered hearing prostheses;" IEEE Transactions on Biomedical Engineering; vol. 64, No. 5; May 2017; 12 Pages.

Wilson, et al. "Global hearing health care: New findings and perspectives;" The Lancet; vol. 390; Dec. 2, 2017; 13 Pages.

Wong, et al. "A comparison of regularization methods in forward and backward models for auditory attention decoding;" Frontiers in Neuroscience; vol. 12, Article 531; Aug. 2018; 16 Pages.

Zink, et al. "Online detection of auditory attention with mobile EEG: Closing the loop with neurofeedback;" bioRxiv; Retrieved from https://www.biorxiv.org/content/10.1101/218727v1; Nov. 13, 2017; 18 Pages.

\* cited by examiner

END-TO-END DEEP NEURAL NETWORK FOR AUDITORY ATTENTION DECODING

CROSS-REFERENCE TO RELATED APPLICATIONS

This application claims the benefit under 35 U.S.C. § 119 of provisional application No. 62/782,766 filed Dec. 20, 2018, which is hereby incorporated by reference herein in its entirety.

STATEMENT REGARDING FEDERALLY SPONSORED RESEARCH

This invention was made with government support under FA8702-15-D-0001 awarded by the United States Air Force. The government has certain rights in the invention.

FIELD

The present disclosure relates to devices, systems, and methods for auditory attention decoding using end-to-end deep neural networks.

BACKGROUND

As is known in the art, hearing loss, and the associated use of hearing aids, is rising among the general population. Despite widespread use of hearing aids, and the incorporation of spatial and spectral algorithms for noise reduction, hearing aids often are considered unsatisfactory in regard to their performance in noisy environments. Particularly when background noise includes multiple acoustic sources (e.g., talkers), hearing aids suffer because they have difficulty separating the "signal" (i.e., an acoustic source of interest to the listener) from the "noise" (i.e., all other acoustic sources) due to similarities in spectro-temporal characteristics. The failure of hearing aids to improve listening ability in complex acoustic environments, either due to poor device performance, or lack of use triggered by poor performance, is associated with social isolation and various forms of cognitive decline such as depression. Therefore, solving the problem of assisted listening in multi-talker environments (i.e., environments with multiple acoustic sources) could have wide societal benefits in terms of communication and mental health.

Auditory attention decoding (AAD) is an approach aimed at separating an acoustic source of interest to the listener ("attended source") from other acoustic sources ("unattended sources"). AAD exploits knowledge of the listener's auditory intent ("attention") to isolate and enhance the desired audio stream and suppress others. Evidence for neural encoding of speech has been shown with various sensing modalities including electroencephalography (EEG), magnetoencephalography (MEG), and electrocorticography (ECoG).

One approach to AAD involves EEG for capturing neural data and uses a linear least-squares method for stimulus (broadband speech envelope) reconstruction and correlation of actual and predicted speech envelopes to identify the attended source. Stimulus reconstruction is also known as the "backward" problem in AAD, as the mapping from EEG to stimulus is the reverse of the natural auditory stimulus/response phenomenon. By contrast, predicting EEG from the stimulus is known as the "forward" problem.

As is known in the art, AAD has been used to make an attention decision between two simultaneous, spatially separated acoustic sources. This approach has also been modified to evaluate: sensitivity to number of EEG channels and size of training data; robustness to noisy reference stimuli; the use of auditory-inspired stimulus pre-processing including subband envelopes with amplitude compression; cepstral processing of EEG and speech signals for improved correlations; the effects of speaker (spatial) separation and additional speech-like background noise; the effects of (simulated) reverberation; and potential performance improvements through various regularization methods.

An AAD system can be constructed as a physical or logical pipeline comprising steps for neural data acquisition, stimulus representation, signal processing (e.g., forward or backward predictive modeling), and attention determination. As mentioned previously, EEG, MEG, and ECoG can serve as neural sensing modalities. In the case of EEG, work has been done to reduce the number of EEG channels in an effort to move toward less obtrusive, portable systems. Speech stimuli have been represented with spectrograms and frequency-dependent envelopes after gammatone filtering. To exploit the power and biological relevance of non-linear processing, effective implementations of the backward model (predicting stimuli from EEG) with neural networks have been shown, and linear versions of the forward model (predicting EEG from the stimuli) have also been described in the art. As an alternative to both forward and backward modeling, canonical correlation analysis, which involves transforming both stimulus and response to maximize mutual projections and thus improve correlations, has been applied to EEG and audio data, both with various filters, to enhance AAD performance. Finally, state-space models have been applied as a final step in AAD systems to smooth noisy attention decisions and allow for near real-time update rates.

Previous attempts at the forward model of AAD generally involve a two-step process. First, neural data is used to reconstruct an auditory envelope. Second, the reconstructed auditory envelope is correlated against a candidate auditory envelope using a technique such as Pearson correlation.

SUMMARY

Described herein techniques and structures for assisted listening in multi-talker environments using end-to-end deep neural networks (DNNs) for auditory attention decoding (AAD). In some embodiments, multi-channel electroencephalogram (EEG) measured from the listener may be used in conjunction with the acoustic envelope of a candidate acoustic source to compute a similarity score using a DNN. The more similar the DNN determines the EEG and the candidate source's envelope, the more likely the listener is attempting to attend to the particular acoustic source. Unlike prior art systems, embodiments of present disclosure can perform EEG-based AAD in a single step. In particular, a single DNN may be used to both (a) reconstruct the auditory envelope from EEG and (b) correlate the reconstructed auditory envelope with the candidate auditory envelope. This approach has the advantage of allowing a non-linear similarity function to be optimized directly relative to a linear decoder due to the inherent non-linear processing of acoustic signals along the auditory pathway.

According to one aspect of the present disclosure, a method can include: receiving neural data responsive to a listener's auditory attention; receiving an acoustic signal responsive to a plurality of acoustic sources; for each of the plurality of acoustic sources: generating, from the received acoustic signal, audio data comprising one or more features of the acoustic source, forming combined data representative of the neural data and the audio data, and providing the combined data to a classification network configured to calculate a similarity score between the neural data and the acoustic source using one or more similarity metrics; and using the similarity scores calculated for each of the acoustic sources to identify, from the plurality of acoustic sources, an acoustic source associated with the listener's auditory attention.

In some embodiments, the method can include separating the acoustic signal into a plurality of candidate signals, wherein generating audio data for an acoustic source comprises generating audio data using one of the plurality of candidate signals associated with the acoustic source. In some embodiments, the method can include receiving one or more neural signals responsive to the listener's brain activity and processing the one or more neural signals to generate the neural data. In some embodiments, a device worn by the listener receives the one or more neural signals is and a companion device calculates the similarity scores.

In some embodiments, the neural data can include multi-channel electroencephalogram (EEG) data. In some embodiments, forming the combined data comprises generating a matrix comprising the neural data and the audio data. In some embodiments, the classification network can be a convolutional deep neural network (DNN). In some embodiments, the convolutional DNN can include at least two convolutional layers and at least three fully connected layers. In some embodiments, using the similarity scores calculated for each of the acoustic sources to identify the acoustic source associated with the listener's auditory attention can include identifying an acoustic source having the highest similarity score.

According to another aspect of the present disclosure, an apparatus can include: a neural sensor interface configured to receive one or more neural signals responsive to a listener's auditory attention; an audio input configured to receive an acoustic signal responsive to a plurality of acoustic sources; and a processor. The processor can be configured to: process the one or more neural signals to generate multi-channel neural data; for each of the plurality of acoustic sources: generate, from the received acoustic signal, audio data comprising one or more features of the acoustic source, form combined data representative of the neural data and the audio data, and provide the combined data to a classification network configured to calculate a similarity score between the neural data and the acoustic source using one or more similarity metrics; and identify, from the plurality of acoustic sources, an acoustic source associated with the listener's auditory attention based on the calculated similarity scores.

In some embodiments, the processor can be configured to separate the acoustic signal into a plurality of candidate signals, and to generate audio data for an acoustic source using one of the plurality of candidate signals associated with the acoustic source. In some embodiments, the apparatus can include an audio output and the processor may be configured to provide, to the audio output, a candidate signal from the plurality of candidate signals corresponding to the acoustic source associated with the listener's auditory attention.

In some embodiments, the neural sensor interface can be configured to receive multi-channel electroencephalogram (EEG) measurements. In some embodiments, the processor may be configured to form the combined data comprises as a matrix comprising the neural data and the audio data. In some embodiments, the classification network may be a convolutional deep neural network (DNN). In some embodiments, the convolutional DNN can include at least two convolutional layers and at least three fully connected layers. In some embodiments, the apparatus can include a non-volatile memory configured to store the DNN as a trained model. In some embodiments, the processor can be configured to identify the acoustic source associated with the listener's auditory attention by identifying an acoustic source having the highest similarity score.

According to another aspect of the present disclosure, a non-transitory computer readable medium can store program instructions that are executable to: receive neural data responsive to a listener's auditory attention; receive an acoustic signal responsive to a plurality of acoustic sources; for each of the plurality of acoustic sources: generate, from the received acoustic signal, audio data comprising one or more features of the acoustic source, form combined data representative of the neural data and the audio data, and provide the combined data to a classification network configured to calculate a similarity score between the neural data and the acoustic source using one or more similarity metrics; and use the similarity scores calculated for each of the acoustic sources to identify, from the plurality of acoustic sources, an acoustic source associated with the listener's auditory attention

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

The drawings are not necessarily to scale, or inclusive of all elements of a system, emphasis instead generally being placed upon illustrating the concepts, structures, and techniques sought to be protected herein.

DETAILED DESCRIPTION

As used herein, the term "processor" generally refers to a collection of hardware and/or software configured to perform and execute the processes, steps, or other functionality described in conjunction therewith.

Figure 1:
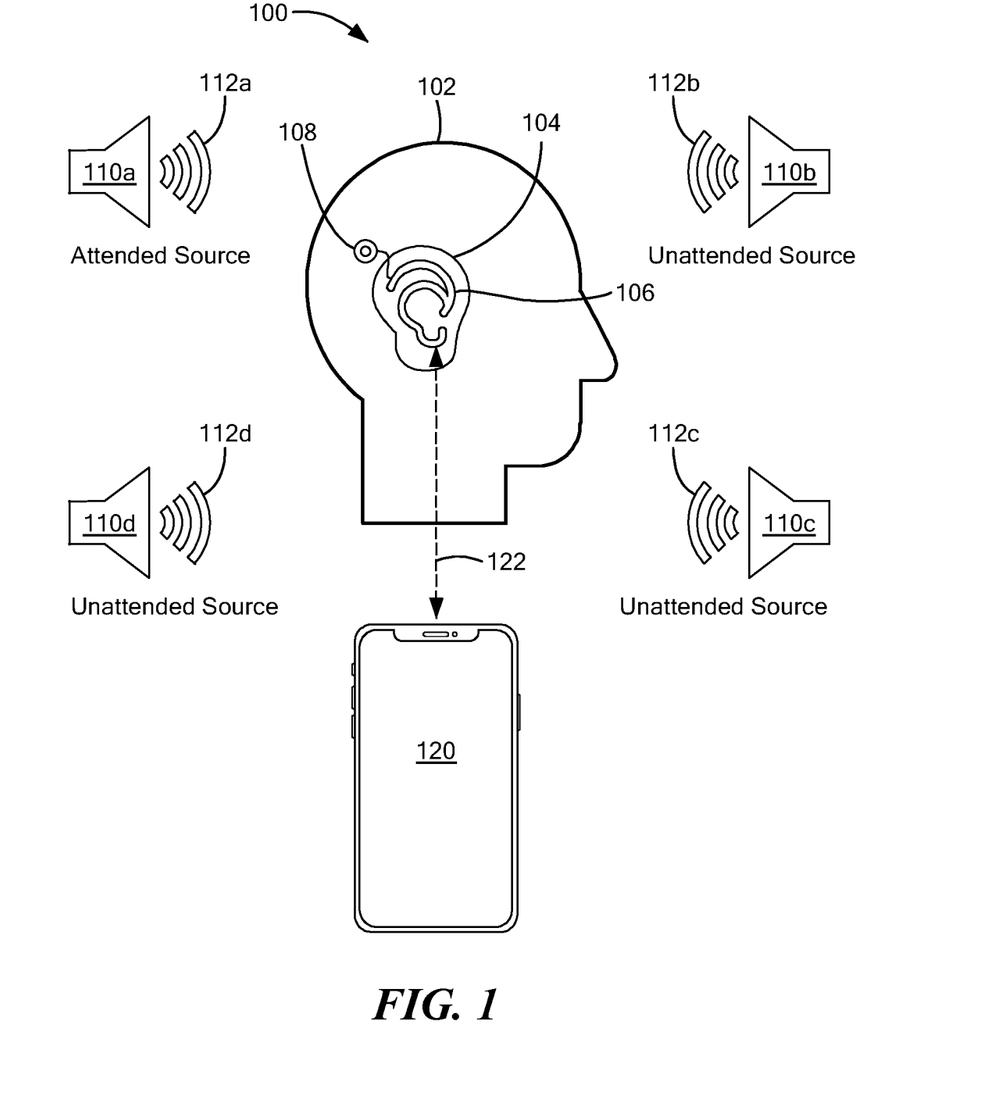
FIG. 1 is a diagram of an illustrative environment in which a listener attends to one acoustic source among multiple candidate sources, according to some embodiments of the present disclosure.

Referring to FIG. 1, an illustrative environment 100 can include a listener (or "user") 102 and a plurality of acoustic sources 110a, 110b, 110c, 110d, etc. (110 generally). One of the acoustic sources 110 may be of interest to the listener, i.e., an attended source, while the remaining acoustic sources 110 may be "noise" to the listener, i.e., unattended sources. For explanatory purposes, a first acoustic source 110a will be herein treated as the attended source and the other sources 110b, 110c, 110d shown in FIG. 1 will be treated as the unattended sources. Examples of acoustic sources 110 include humans ("talkers"), animals, environment noise, loudspeakers, and musical tracks/parts. The acoustic sources (also referred to herein as the "candidate sources") 100 can be in any spatial orientation relative to the speaker 102 and the spatial orientation shown in FIG. 1 is merely illustrative. Acoustic sources 110a, 110b, 110c, 110d can produce respective audio streams (or "waves") 112a, 112b, 122c, 112d (112 generally). A particular audio stream 112 may carry, for example, a stream of speech or a stream of music.

While four acoustic sources 110 are shown in FIG. 1, the concepts and structures sought to be protected herein can be applied to environments having an arbitrary number of acoustic sources. Moreover, while the acoustic sources 110 are illustrated in FIG. 1 as being spatially separated, the concepts and structures sought to be protected herein can be used for AAD among co-located acoustic sources. For example, two or more of acoustic sources 110 may correspond to a single loudspeaker from which multiple human speakers or multiple musical tracks/parts are played.

A listener device 106 may be worn by the listener 102, carried by the listener 102, or otherwise located proximate to the listener 102. In the example of FIG. 1, listener device 106 may be placed in or about the listener's ear 104. In some embodiments, listener device 106 may be a hearing aid or a cochlear implant. In some embodiments, a listener may wear multiple devices (e.g., two hearing aids) configured to work in coordination to perform AAD according to the techniques disclosed herein.

One or more neural sensors 108 may be attached to the listener 102 and electrically coupled to the listener device 102. Neural sensors 108 may be configured to generate one or more signals ("neural signals") responsive to the listener's brain activity. As described in detail below, the neural signals can be processed to generate structured data ("neural data") suitable for input to a DNN. Neural sensors 108 can include, for example, electrodes attached to or located proximate to the listener's scalp. In some embodiments, neural sensors 108 can include a plurality of EEG electrodes (either "wet" or "dry" electrodes) configured to generate multi-channel EEG data responsive to the listener's brain activity (e.g., by sensing EEG signals at multiple locations on the listener's head). In some embodiments, neural sensors 108 may be integrated into the listener device 102. For example, listener device 106 may include one or more electrodes situated such that when the device 106 is worn by the listener 102, the electrodes are capable of sensing brain activity. In some embodiments, neural sensors 108 may be integrated into a headband, hat, eyeglasses, or other head-worn article. In some embodiments, neural sensors 108 can be wirelessly coupled to listening device 108.

While various embodiments are described herein as using neural measurements to perform AAD (and, in some cases, using EEG measurements), the concepts and structures sought to be protected herein can be practiced using other measures of biological function, including but not limited to MEG, ECoG, electro-oculagraphy (EOG), electromyography (EMG), accelerometry, infrared spectroscopy. In some embodiments, two or more such measures of biological function may be used to perform AAD.

Listener device 106 can include one or more microphones configured to convert the audio streams 112a, 112b, 112c, 112d, etc. into an acoustic signal (referred to herein as the "received acoustic signal"). Thus, the received acoustic signal may be responsive to several candidate sources 110. As discussed in detail below, the received acoustic signal can be separated into a plurality of signals ("candidate signals"), each responsive to a single candidate source 110. A particular candidate signal can then be processed to generate structured data ("audio data") that includes features of the corresponding source 110. As further described below, the audio data for a particular candidate source 110 can be combined with the neural data, and the combined data can be provided as input to a DNN configured to score how similar the candidate source is to the listener's attended source. Multiple similarity scores (e.g. one for each candidate source 110) can be compared to identify the attended source 110a from among multiple candidate sources 110a, 110b, 110c, 110d, etc. In some embodiments, listener device 110 may then output the candidate signal corresponding to the identified attended source 110a. For example, listener device 110 may include a loudspeaker to convert the candidate signal into sound waves such that the attended source 110a can be more readily heard by the listener 102 over the unattended sources 110b, 110c, 110d (i.e., over the noise). In some embodiments, listener device 110 is configured to enhance the attended audio stream 112a and suppress the unattended streams 112b, 122c, 122d.

In some embodiments, a companion device 120 may be provided to perform at least some of the processing described herein. For example, listening device 106 may perform tasks that are relatively inexpensive (e.g., in terms of computational resources), such as audio pre-processing, while offloading relatively expensive tasks, such as computing similarity scores using DNNs, to companion device 120. Companion device 120 can be, for example, a smartphone, a smartwatch, a tablet, or other type of portable or wearable computing device. Companion device 120 may be communicably coupled to listener device 106 via a wired or wireless communication link 122. As one example, listener device 106 may include BLUETOOTH adapter configured to communicate with companion device 120. In some embodiments, companion device 120 may have greater processing and/or storage capability relative to listener device 106. In some embodiments, some of the processing disclosed herein can be performed on a remote server and/or within a cloud computing environment.

In some embodiments, companion device 120 may be configured to run an application (or "app") that operates in coordination with listener device 106 to improve the accuracy of the AAD techniques disclosed herein. For example, the app may provide a user interface (UI) for the listener 102 to enter biometric information, such as age, gender, and weight information, along with clinical information related to the listener's hearing capability and hearing loss. The app can use this information to tune a DNN model for a particular listener with the goal of improving AAD accuracy for that listener. The companion device 120 may also be used to provide real time biofeedback to the person and a channel for feedback from the listener to the device. For example, companion device 120 can display or otherwise indicate to what acoustic source and how strongly the listener is attending, and may allow the listener to correct, teach, or override the algorithm or algorithm's decision for the attended source (e.g., the attended talker). As another example, companion device 120 may identify the attended source (e.g., the attended speaker) and/or determine the spatial location of the attended source.

Figure 2:
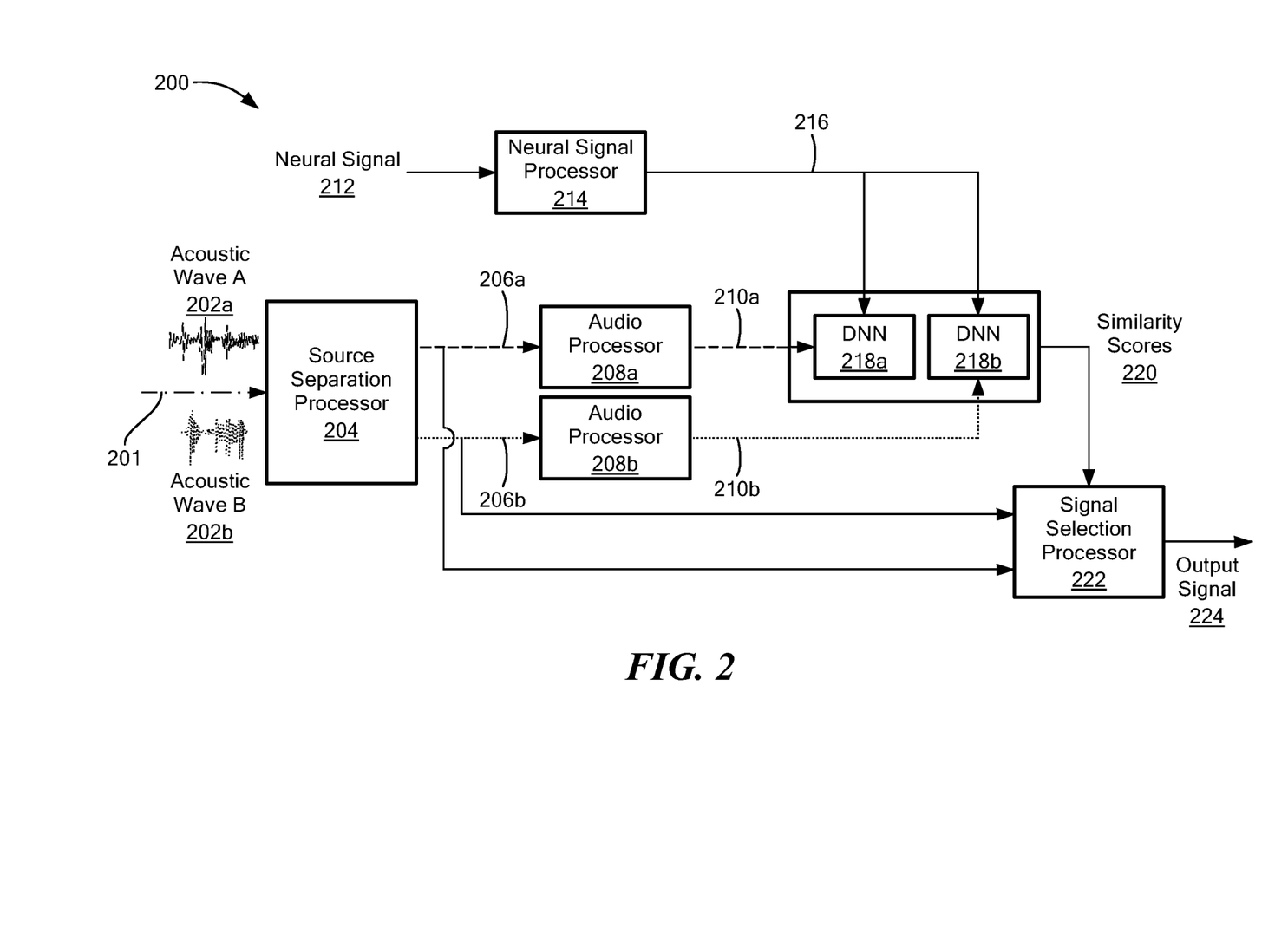
FIG. 2 is a block diagram of an illustrative system for auditory attention decoding (AAD) using deep neural networks (DNNs), according to some embodiments of the present disclosure.

FIG. 2 shows an illustrative system 200 for auditory attention decoding (AAD), according to an embodiment of the present disclosure. In some embodiments, system 200 may be implemented (in whole or in part) within a listener device, such as listener device 106 of FIG. 1. In some embodiments, system 200 may be implemented (in whole or in part) within a companion device, such as companion device 120 of FIG. 1.

An acoustic signal 201 may be received from, for example, a microphone or other audio input of the listener/companion device. The received acoustic signal 201 may be responsive to audio streams 202a, 202b, etc. (202 generally) received from a plurality of candidate sources. One of the audio streams (e.g., stream 202a) may correspond to an attended source, while the other audio streams (e.g., stream 202b) may correspond to unattended sources. As explained below, the system 200 is configured to identify the attended source from among multiple candidate sources. While only two candidate sources are illustrated in FIG. 2 (i.e., the sources corresponding to audio streams 202a and 202b), the systems and techniques disclosed herein can be applied to an arbitrary number of candidate sources, as discussed further below.

The system 200 includes a source separation processor 204 configured to separate the received acoustic signal 201 into a plurality of candidate signals 206a, 206b, etc. (206 generally). Examples of source separation algorithms include spectrally based techniques, time domain based techniques, and beamforming (sometimes referred to as spatial angle) techniques, which may be used in combination. Spectral techniques—such as described in Belouchrani, A., Amin, M. G. On the Use of Spatial Time Frequency Distributions for Signal Extraction. Multidimensional Systems and Signal Processing 9, 349-354 (1998)—may use cues in the signal to create an ideal binary mask on the spectrogram and reconstruct clean signals in this manner. Time domain techniques—such as described in Conv-Tas-Net: Surpassing Ideal Time-Frequency Magnitude Masking for Speech Separation Y Luo, N Mesgarani IEEE/ACM Transactions on Audio, Speech, and Language Processing 27 (8), 1256-1266, 2019—may operate on the waveform directly and stitch together cleaned segments. Beamforming techniques capitalize on the difference in spatial location of sources and use multiple microphones. Candidate signal 206a, 206b are responsive to audio streams 202a, 202b, respectively.

The system 200 further includes a plurality of audio processors 208a, 208b, etc. (208 generally) each configured to receive a candidate signal 206 from source separation processor 204 and to perform one or more audio pre-processing techniques. It should be understood that, within the illustrative system 200, signals/data may be passed/transferred between different components using one or more signal/data paths. Examples of such signal/data paths are shown as directed lines in FIG. 2. For example, candidate signal 206a may be passed from source separation processor 204 to audio processor 208a via a signal path represented by line 206a. Such signal/data paths may correspond to physical wires or to logical data paths (e.g., computer instructions operable to transfer data between different software components).

An audio processor 208 may use one or more audio processing techniques to generate, from a received candidate signal 206, audio data 210 that includes one or more features of the corresponding candidate source. For example, audio data 210 may represent an audio envelope or other time or frequency or multi-dimensional transform of the audio data of the candidate source. As additional examples, audio data 210 may represent pitch and/or formant trajectories of the candidate source. In some embodiments, an audio processor 208 can include an analog-to-digital converter (ADC) to convert an analog input signal 206 to a digital signal, and one or more digital signal processors (DSPs) to operate on the digital signal. The generated audio data 210 may be structured such that it can be readily combined with neural data and provided as input to a DNN, as described further below.

The system 200 further includes a neural signal processor 214 configured to receive one or more neural signals 212 responsive to a listener's brain activity. The neural signals 212 may be received from one or more sensors (e.g., electrodes) attached to the listener. In some embodiments, neural signals 212 correspond to multi-channel EEG measurements. Neural signal processor 214 can generate, as output, time series neural data 216. Processor 214 might apply a variety of signal transformation steps to facilitate downstream computation. These transformation steps may include some combination of source localization, bandpass filtering, and artifact rejection as examples. The generated neural data 216 may be structured such that it can be readily combined with audio data 210 and provided as input to a DNN. For example, neural data 216 may be a matrix, where each row of the matrix includes a time series of EEG measurements obtained from a distinct EEG channel.

The system 200 further includes a plurality of DNNs 218a, 218b, etc. (218 generally), one for each of the acoustic sources. A given DNN 218 may receive as input, neural data 216 generated by the neural signal processor 214 and audio data 210 generated by a corresponding one of the audio processors 208. The neural and audio data may be combined into a structure referred to herein as the "combined data." For example, as shown in FIG. 2, a first DNN 218a may receive combined data comprising neural data 216 and first audio data 210a generated by a first audio processor 208a, whereas a second DNN 218b may receive combined data comprising the (same) neural data 216 and second (different) audio data 210b generated by a second audio processor 208b. In some embodiments, neural data 216 and audio data 210 may be combined into a single matrix of multi-dimensional time series data suitable for input to a DNN 218, as discussed further below in the context of FIG. 3.

A particular DNN 218 may be configured to reconstruct an audio envelope from the neural data 216 (i.e., an audio envelope corresponding to the listener's auditory attention) and to correlate the reconstructed auditory envelope with an audio envelope encoded within the candidate audio data 210. A DNN 218 can function as a non-linear similarity function to be optimized directly relative to a linear decoder due to the inherent non-linear processing of acoustic signals along the auditory pathway. As output, a DNN 218 may provide a numerical value (referred to herein as a "similarity score") indicating how similar the candidate audio envelope is to reconstructed audio envelope. Thus, a similarity score indicates how likely it is that a particular candidate source is the listener's attended source. The system 200 may compute multiple similarity scores 220 (e.g., one for each candidate source), and the multiple scores 220 may be used to identify the determine which candidate source is most probably the attended source. A particular DNN 218 may be trained on a per-listener basis or trained using average weights across a group or population of listeners. One or more DNNs 218 can trained ahead of time (e.g., in a laboratory setting) and then loaded onto a listener/companion device for use in real-time AAD.

Signal selection processor 222 can receive the similarity scores 220 computed by the DNNs (e.g., one similarity score for each candidate source) and, based on these scores, determine which candidate source corresponds to the attended source. In some embodiments, signal selection processor 222 can identify the candidate source as the source which has the largest corresponding similarity score 220. Signal selector 220 can provide, as output, an output signal 224 responsive to the candidate signal 206 of the attended source. Thus, for example, if audio stream 202a in FIG. 2 is the attended source, signal selection processor 222 can output the corresponding candidate signal 206a as the output signal 224. In some embodiments, output signal 224 may be passed to an audio output device (e.g., a loudspeaker within the listening/companion device) to assist with hearing of that attended source.

It should be understood that the plurality of DNNs 218 can be provided using a common set of hardware and/or software resources. In the case of software-implemented DNNs, the plurality of DNNs 218 may correspond to multiple instances of a common software component (e.g., multiple object instances of the same class). Multiple DNNs 218 may each use the same trained model or may use different trained models. An illustrative convolutional architecture that may be used within one or more of the DNNs 218 is shown in FIG. 3 and described below in the context thereof.

While FIG. 2 shows a system 200 having only two acoustic sources, it should be appreciated that the concepts and structures sought to be protected herein can be used for AAD among an arbitrary number of candidate sources. In general, for N candidate sources, the system 200 of FIG. 2 can have N candidate signal paths 206, N audio processing blocks 208, N audio data paths 210, and N DNNs 218. Thus, FIG. 2 illustrates a system architecture that can be generalized to any number of acoustic sources.

It is appreciated herein that using a separate DNN 218 for each candidate source allows the system 200 to naturally extend to any number of candidate sources. In particular, the disclosed architecture allows for use of a single trained DNN model having a fixed-size input, namely a single stream of audio data paired with neural data. In some embodiments, a single set of DNN "weights" can be used, regardless of the number of candidate sources. This approach can reduce costs and complexity compared to alternative approaches where a DNN is trained to choose between a fixed number of acoustic sources (e.g., exactly two sources) or a maximum number of sources (e.g., no more than M sources). For example, the disclosed architecture can reduce processing and storage requirements within the listening and/or companion devices, as well as reducing bandwidth usage between the listening and companion devices. Moreover, the disclosed architecture can reduce the time required to train new DNN models for individual users (i.e., listeners) or populations of users.

Figure 3:
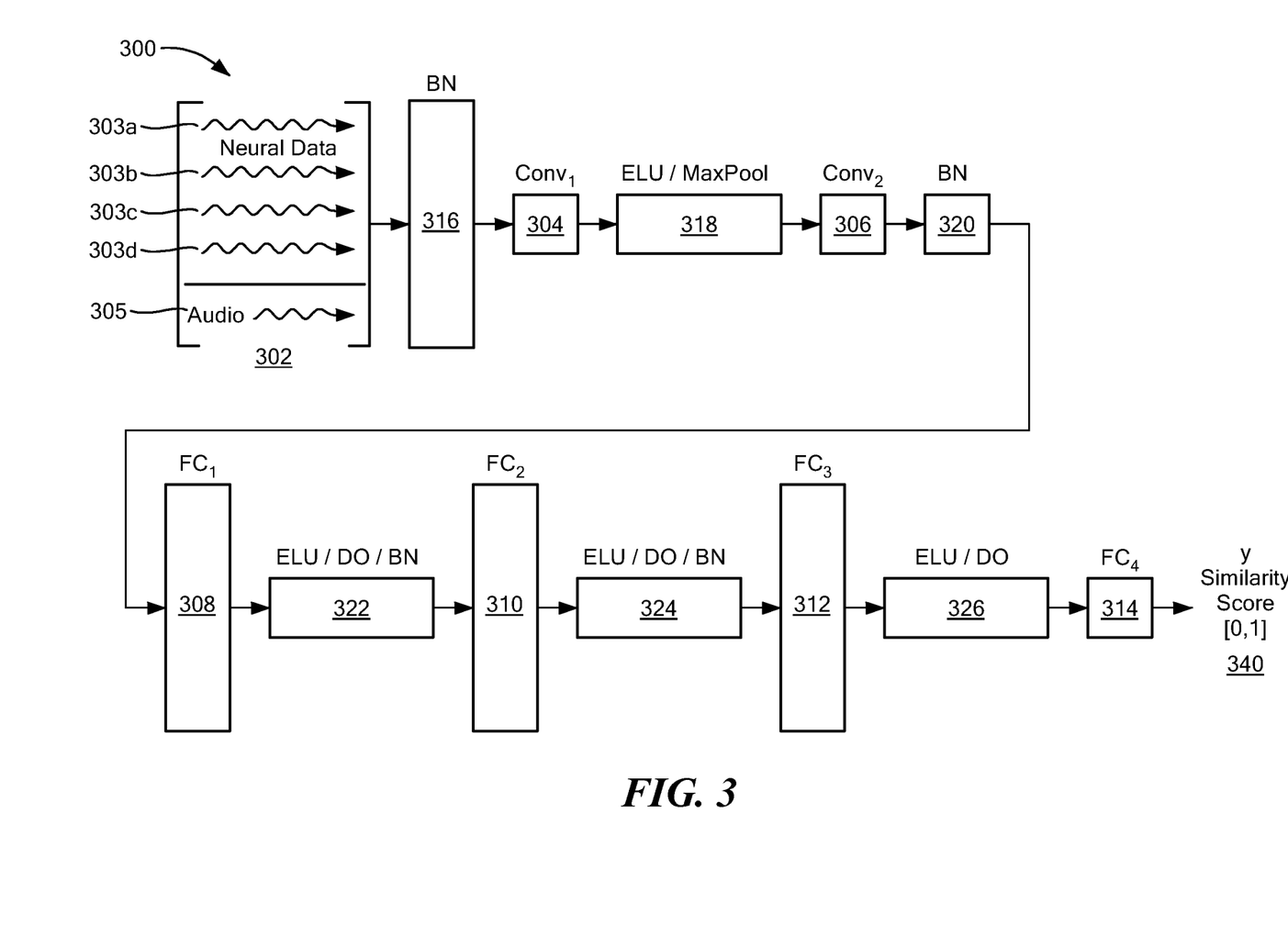
FIG. 3 is a block diagram of an illustrative convolution network architecture that can be used for AAD, according to some embodiments of the present disclosure.

Turning to FIG. 3, a convolution network architecture (or "network") 300 can be used for AAD, according to some embodiments. The illustrative network 300 can be used, for example, within one or more of the DNNs 218 shown in FIG. 2 and described above.

The network 300 can receive input 302 comprised of multi-channel neural data 303 and audio data 305. In the example of FIG. 3, the input 302 includes four channels of neural data 303a, 303b, 303c, 303d (303 generally), however this number is merely illustrative and generally any number of channels of neural data can be used. The neural data 303 and audio data 305 may be time series data arranged into a matrix, with one row of audio data 305 concatenated to multiple rows of neural data 305a, 305b, etc.

The illustrative network 300 can include a first convolution layer ($Conv_1$) 304, a second convolution layer ($Conv_2$) 306, and four fully connected layers ($FC_1$) 308, ($FC_2$) 310, ($FC_3$) 312, ($FC_4$) 314. In some embodiments, $Conv_1$ may have a kernel size of three and $Conv_2$ may have a kernel size of one. In some embodiments, $Conv_1$ may have 65 input channels and 64 output channels, and $Conv_2$ may have 64 input channels and 2 output channels. In other embodiments, $Conv_1$ may have 19 input channels and 19 output channels, and $Conv_2$ may have 19 input channels and 2 output channels.

The fully connected layers 308, 310, 312, 314 may decrease in size such that $FC_1 \geq FC_2 \geq FC_3 \geq FC_4$. In one example, $FC_1$ may have 246 inputs and 200 outputs, $FC_2$ may have 200 inputs and 200 outputs, $FC_3$ may have 200 inputs and 100 outputs, and $FC_4$ may have 100 inputs and 1 output. In FIG. 3, the number of inputs to $FC_1$ may appear greater than the number of outputs from $Conv_2$ and BN 320. However, the data cube is reshaped between the BN block 320 and $FC_1$ block 308 such that the total number of elements is preserved while the number of channels decreases (e.g., to one) and the number of inputs increases.

The convolutional and fully connected layers may be interconnected via one or more components, such as batch normalization layers (BNs), exponential linear units (ELUs), drop-outs (DOs), and/or max pooling layers (MaxPools). Batch normalization layers help with keeping the data well scaled for subsequent multiplications. Exponential linear units are one example of a mathematical operation that makes the whole DNN a non-linear transform of the input data. An alternative activation might be a sigmoid activation or a rectified linear unit. Drop out acts as a form of regularization that is used only during training in order to facilitate generalization of the DNN to unseen data. Max pooling operations are another example of a mathematical operation that makes the whole DNN a non-linear transform and also act as a data reduction by summarization technique. Other examples might be median or minimum pooling. For example, as shown in FIG. 3, input 302 can be connected to $Conv_1$ 304 via a BN layer 316; $Conv_1$ 304 can be connected to $Conv_2$ 306 via an ELU or a MaxPool 318; $Conv_2$ 306 can be connected to $FC_1$ 308 via a BN 320; $FC_1$ 308 can be connected to $FC_2$ 310 via an ELU, DO, or BN 322; $FC_2$ 310 can be connected to $FC_3$ 312 via ELU, DO, or BN 324; and $FC_3$ 312 can be connected to $FC_4$ 314 via an ELU or a DO 326.

In some embodiments, network 300 can be trained using a binary cross-entropy loss function, a batch size of 1024, an Adam optimizer, no weight decay, and a learning rate of $10^{-3}$. In some embodiments, the training (or "optimization") process can be terminated if the loss on the training set declines to below 0.09 or if the optimizer has run for at least 2400 steps. It should be understood that these training parameters are merely illustrative and that other training parameters can be used.

Training can be performed for individual listeners (or "subjects") or for an "average listener" out of a given population. In some embodiments, training may proceed as follows. First, multiple sources of audio data are presented to a subject and, for each source, the subject's neural response data (e.g., EEG data) is recorded. Second, for each source, the presented audio data and the recorded neural response data are concatenated to form a DNN input 302. The concatenation can be performed after each source's audio data is converted into a data matrix for the algorithm estimation to avoid discontinuities. Third, the (non-linear) DNN estimator 300 is trained (i.e., the weights within the various network components are adjusted) so as to reconstruct the attended source using the audio data and neural response data.

The operation of the convolutional DNN 300 can be better understood by examining the filter weights of the first convolutional layer $Conv_1$. Essentially, this convolution is creating a set of linear combinations of the neural data 303 and audio data 305. The full convolutional weight matrix can be 3-dimensional (kernel by input channel by output channel), but can be collapsed into one dimension in order to visualize it. First, the middle element of the three-point temporal kernel can be selected, and then the absolute value of the weights can be taken. Next, the convolutional weights can be summed along the input channel. Taking wet EEG as an example, there are 64 EEG channels and an audio channel as the input, and 64 channels as the output from the first convolutional layer. $Conv_1$. The 64 EEG weights of the 65-element vector can be renormalized so that the minimum weight is 0 and the maximum weight is 1. This normalization can then be applied to the 65th audio element. The normalization can be computed separately for different types of neural data (e.g., wet EEG vs. dry EEG) and on a per-subject basis.

In the case where training is done for an "average" listener, weights can be computed for multiple subjects and then averaged together. The averaged weights can be re-normalized so that the minimum weight is 0 and the maximum weight is 1.

Figure 4:
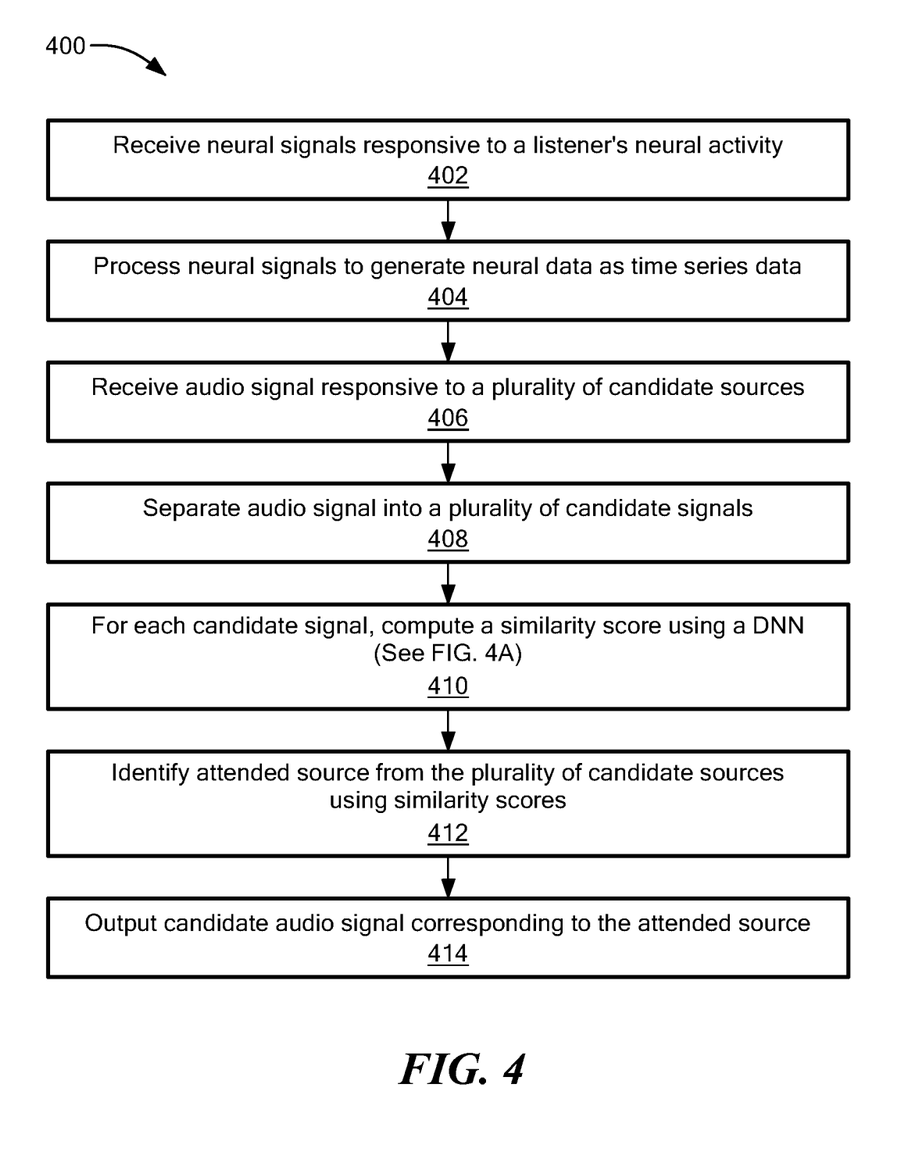
FIGS. 4 and 4A are flow diagrams showing illustrative processing for AAD using end-to-end DNNs, according to some embodiments of the present disclosure.
Figure 4A:
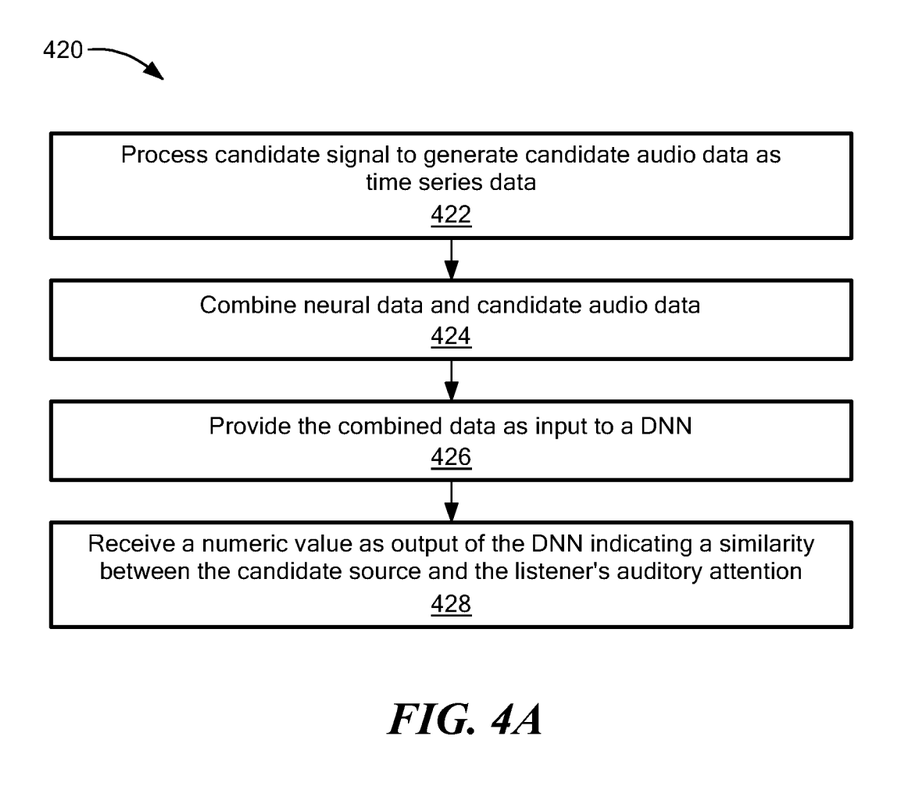

FIGS. 4 and 4A show processes 400, 420 for auditory attention decoding, according to some embodiments of the present disclosure. The illustrative processes 400, 420 can be executed by a listener device (e.g., listener device 106 of FIG. 1) or a companion device (e.g., companion device 120 of FIG. 1). In some embodiments, portions of the processing shown in FIGS. 4 and 4A may be executed by a listener device while other portions may be executed by a companion device operating in communication and coordination with the listener device.

At block 402, one or more neural signals may be received responsive to a listener's neural activity. More particularly, when the listener is exposed to one or more acoustic sources, the neural signals may be responsive to the listener's auditory attention. In some embodiments, the neural signals may be received from one or more neural sensors (e.g., wet or dry EEG electrodes) attached to, or otherwise in contact with, the listener. In some embodiments, at least two EEG electrodes are used, providing multiple channels of EEG.

At block 404, the neural signals may be processed to generate neural data as time series data. In the case of where multiple neural sensors are used, the generated neural data may comprise multi-channel time series data. In some embodiments, the generated neural data may be in matrix form. Examples of techniques for processing neural signals into structured neural data are described above in the context of neural signal processor 214 of FIG. 2.

At block 406, an audio signal responsive to a plurality of candidate sources may be received. The audio signal may be received, for example, via a microphone within the listener or companion device. At block 408, the received audio signal may be separated into a plurality of candidate signals. Examples of techniques for separating out the candidate signals are described above in the context of source separation processor 204 of FIG. 2. In some embodiments, multiple audio signals can be received, for example, using two or more different microphones. Each of the audio signals can be separated and processed according to the techniques disclosed herein.

At block 410, for each candidate source, a similarity score can be computed using a DNN according to the processing 420 of FIG. 4, which is described in detail below. In particular, for each source, a DNN can be used to reconstruct an audio envelope from the neural data and to determine how similar the reconstructed envelope is to the candidate signal's envelope. For N acoustic sources, N similarity scores may be computed. At block 412, an attended source can be identified from among the candidate sources using the similarity scores. In some embodiments, the candidate source having the highest similarity score is identified as the attended source.

At block 414, the candidate signal corresponding to the attended source can be provided as an output signal. For example, the candidate signal may be passed to a loudspeaker within the listening or companion device. Thus, process 400 can be used to assist listeners with hearing an acoustic source of interest over other acoustic sources (i.e., "noise").

Turning to FIG. 4A, a process 420 can be used to compute a similarity score between a candidate source and neural data responsive to a listener's auditory attention. At block 422, a candidate signal (i.e., a signal separated from a received audio signal and corresponding to a particular candidate source) may be processed to generate candidate audio data representing the candidate signal's envelope. Examples of techniques for processing a candidate signal into time series audio data are described above in the context of audio processors 208 of FIG. 2.

At block 424, the candidate audio data may be combined with neural data (e.g., neural data generated at block 404 of FIG. 4) to form an input to the DNN. In some embodiments, the candidate audio data, in vector form, may be concatenated to a matrix of multi-channel neural data.

At block 426, the combined data may be provided as input to a DNN. In some embodiments, the DNN may have a network architecture that is the same as or similarity to network 300 of FIG. 3. The DNN may be trained on a per-listener basis, or for an average listener, using techniques disclosed above in the context of FIG. 3.

At block 428, a similarity score can be received as output of the DNN. The similarity score, computed based on the multi-channel neural data and the candidate audio data, indicates a similarity between the candidate source and the listener's auditory attention. More particularly, the DNN may be configured to reconstruct an audio envelope from the neural data and to compute a similarity between the reconstructed envelope and the candidate signal's envelope represented by the audio data. Multiple similarity scores can be computed (e.g., one per candidate source) and used to identify the attended source, as previously discussed.

Figure 5:
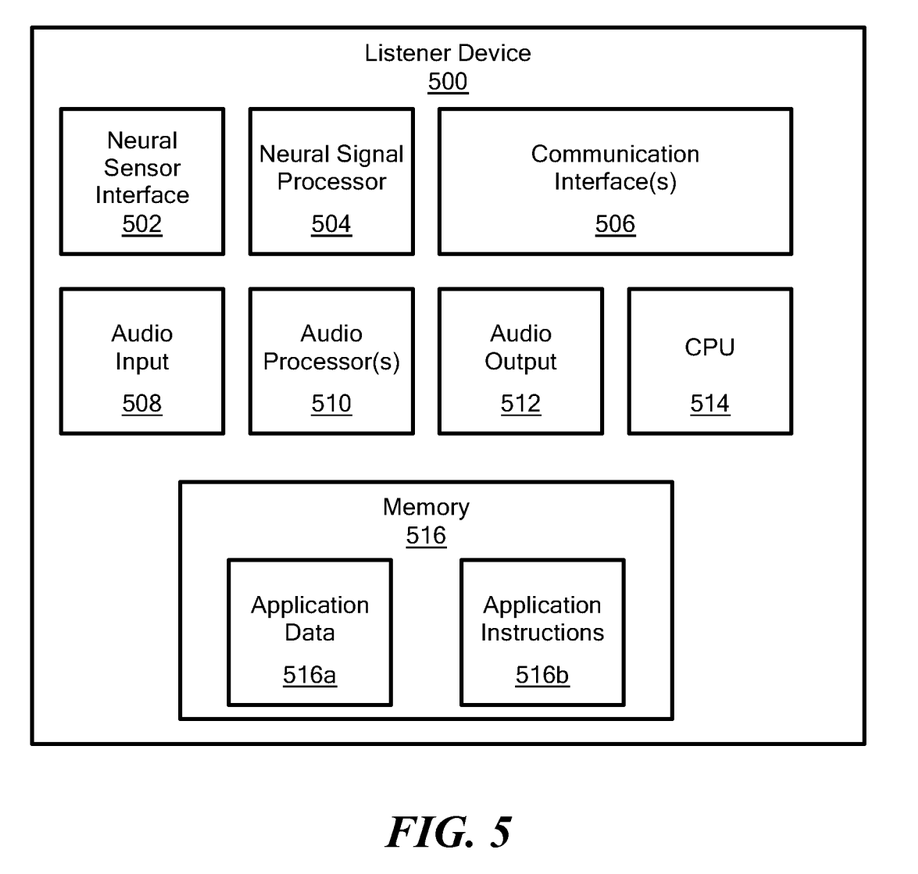
FIG. 5 is a block diagram of an illustrative listening device, according to some embodiments of the present disclosure.

FIG. 5 shows a listening device 500, according to some embodiments of the present disclosure. The illustrative listening device 500 can include a neural sensor interface 502, a neural signal processor 504, one or more communication interfaces 508, an audio input 510, one or more audio processors 512, an audio output 516, a central processing unit (CPU), and memory 518. The neural sensor interfaces 502 can include, for example, EEG electrode interfaces. Neural signal processor 504 can be the same as or similarity to processor 214 of FIG. 2. Communications interfaces 506 can include, for example, BLUETOOTH or other wireless communication interfaces configured for communication with a companion device. Audio input 508 can include, for example, a microphone. Audio processors 510 may be the same as or similar to audio processors 208 of FIG. 2. Audio output 512 can include, for example, a loudspeaker. Memory 516 can be configured to store application data 516a and application instructions 516b. Application instructions can include computer code executable by the CPU 514 to perform AAD using DNNs, according to embodiments of the disclosure. Application data 516a can include data used for AAD, including trained DNN models. In other embodiments, one or more of the components shown in FIG. 5 may be provided within a companion device that operates in communication and coordination with listening device 500. In some embodiments, device 500 can include a graphics processing unit (GPU) used to perform DNN processing or other processing disclosed herein.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or another unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of nonvolatile memory, including by ways of example semiconductor memory devices, such as EPROM, EEPROM, flash memory device, or magnetic disks. The processor and the memory can be supplemented by, or incorporated in, special purpose logic circuitry.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. Therefore, the claims should be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method comprising:
receiving neural data responsive to a listener's auditory attention;
receiving an acoustic signal responsive to a plurality of acoustic sources;
for each of the plurality of acoustic sources:
generating, from the received acoustic signal, audio data comprising one or more features of the acoustic source,
forming combined data representative of the neural data and the audio data, and
providing the combined data to a convolutional deep neural network (DNN) configured to calculate a similarity score between the neural data and the acoustic source using one or more similarity metrics; and
using the similarity scores calculated for each of the acoustic sources to identify, from the plurality of acoustic sources, an acoustic source associated with the listener's auditory attention.

2. The method of claim 1, comprising separating the acoustic signal into a plurality of candidate signals, wherein generating audio data for an acoustic source comprises generating audio data using one of the plurality of candidate signals associated with the acoustic source.

3. The method of claim 1, comprising:
receiving one or more neural signals responsive to brain activity of the listener; and
processing the one or more neural signals to generate the neural data.

4. The method of claim 3, wherein a device worn by the listener receives the one or more neural signals is and a companion device calculates the similarity scores.

5. The method of claim 1, wherein the neural data comprises multi-channel electroencephalogram (EEG) data.

6. The method of claim 1, wherein forming the combined data comprises generating a matrix comprising the neural data and the audio data.

7. The method of claim 1, wherein the convolutional DNN comprises at least two convolutional layers and at least three fully connected layers.

8. The method of claim 1, wherein using the similarity scores calculated for each of the acoustic sources to identify the acoustic source associated with the listener's auditory attention comprises identifying an acoustic source having the highest similarity score.

9. An apparatus comprising:
a neural sensor interface configured to receive one or more neural signals responsive to a listener's auditory attention;
an audio input configured to receive an acoustic signal responsive to a plurality of acoustic sources; and
a processor configured to:
process the one or more neural signals to generate multi-channel neural data;
for each of the plurality of acoustic sources:
generate, from the received acoustic signal, audio data comprising one or more features of the acoustic source,
form combined data representative of the neural data and the audio data, and
provide the combined data to a convolutional deep neural network (DNN) configured to calculate a similarity score between the neural data and the acoustic source using one or more similarity metrics; and
identify, from the plurality of acoustic sources, an acoustic source associated with the listener's auditory attention based on the calculated similarity scores.

10. The apparatus of claim 9, wherein the processor is configured to separate the acoustic signal into a plurality of candidate signals, and to generate audio data for an acoustic source using one of the plurality of candidate signals associated with the acoustic source.

11. The apparatus of claim 10, comprising an audio output, the processor configured to provide, to the audio output, a candidate signal from the plurality of candidate signals corresponding to the acoustic source associated with the listener's auditory attention.

12. The apparatus of claim 9, wherein the neural sensor interface is configured to receive multi-channel electroencephalogram (EEG) measurements.

13. The apparatus of claim 9, wherein the processor is configured to form the combined data comprises as a matrix comprising the neural data and the audio data.

14. The apparatus of claim 9, wherein the convolutional DNN comprises at least two convolutional layers and at least three fully connected layers.

15. The apparatus of claim 9, comprising a non-volatile memory configured to store the DNN as a trained model.

16. The apparatus of claim 9, wherein the processor is configured to identify the acoustic source associated with the listener's auditory attention by identifying an acoustic source having the highest similarity score.

17. A non-transitory computer-readable medium storing program instructions that are executable to:
receive neural data responsive to a listener's auditory attention;
receive an acoustic signal responsive to a plurality of acoustic sources;
for each of the plurality of acoustic sources:
generate, from the received acoustic signal, audio data comprising one or more features of the acoustic source,
form combined data representative of the neural data and the audio data, and
provide the combined data to a convolutional deep neural network (DNN) configured to calculate a similarity score between the neural data and the acoustic source using one or more similarity metrics; and
use the similarity scores calculated for each of the acoustic sources to identify, from the plurality of acoustic sources, an acoustic source associated with the listener's auditory attention.

* * * * *